(12) United States Patent
Lee

(10) Patent No.: US 6,314,058 B1
(45) Date of Patent: Nov. 6, 2001

(54) HEALTH WATCH

(76) Inventor: Byung Hoon Lee, #7-402, Jinhung Apt., 65, Cheongdam-dong, Kangnam-ku, Seoul, 135-100 (KR)

( * ) Notice: Subject to any disclaimer, the term of this patent is extended or adjusted under 35 U.S.C. 154(b) by 0 days.

(21) Appl. No.: 09/189,820

(22) Filed: Nov. 10, 1998

(30) Foreign Application Priority Data

Nov. 21, 1997 (KR) .................................................. 97-61849

(51) Int. Cl.⁷ ............................ G04B 47/06; A61B 5/024
(52) U.S. Cl. ............................ 368/10; 600/500; 600/503
(58) Field of Search .............................. 368/10; 600/494, 600/485, 500, 503; 340/573.1, 449

(56) References Cited

U.S. PATENT DOCUMENTS

| | | | |
|---|---|---|---|
| 4,224,949 | * | 9/1980 | Cramer et al. ........................ 600/503 |
| 4,230,127 | | 10/1980 | Larson . |
| 4,337,529 | * | 6/1982 | Morokawa .............................. 368/10 |
| 4,407,295 | | 10/1983 | Steuer et al. . |
| 4,469,107 | * | 9/1984 | Asmar et al. ........................ 600/494 |
| 4,809,700 | | 3/1989 | Castelli . |
| 4,819,860 | * | 4/1989 | Hargrove et al. ..................... 600/483 |
| 4,896,676 | * | 1/1990 | Sasaki .................................. 600/494 |
| 5,771,001 | * | 6/1998 | Cobb .................................. 340/573.1 |
| 5,894,454 | * | 4/1999 | Kondo .................................... 368/10 |

FOREIGN PATENT DOCUMENTS

| | | |
|---|---|---|
| 62-109471 | 11/1988 | (JP) . |
| 2-17170 | 9/1991 | (JP) . |
| 2-249207 | 4/1992 | (JP) . |
| 79-3989 | 4/1985 | (KR) . |

\* cited by examiner

*Primary Examiner*—Andrew H. Hirshfeld
*Assistant Examiner*—Jeanne-Marguerite Goodwin
(74) *Attorney, Agent, or Firm*—Thomas C. Feix

(57) ABSTRACT

A health watch is disclosed which has various functions such as atmospheric air thermometer, body thermometer, cardiac beat meter, displaying of beating sound waves, display of cardiac beating sounds, blood pressure meter and the like. An IC counting element is provided for each of the functions, and a plurality of display windows are provided to display the respective measured data. For this purpose, sensors are installed on the watch in contact with the wrist. Thus the various functions are combined in one wrist watch, so that a convenience would be ensured by eliminating the troubles of carrying and storing the various conventional separate health checking devices. Therefore, one's own health state can be checked at any place, thereby making it possible to prevent assault of any disease.

11 Claims, 3 Drawing Sheets

HEALTH WATCH

BACKGROUND OF THE INVENTION

1. Field of the Invention

The present invention relates to a health watch which has various functions such as atmospheric air thermometer, body. thermometer, cardiac beat meter, displaying of beating sound waves, cardiac beating sounds, blood pressure meter and the like.

2. Description of the Prior Art

The conventional wrist watch has the function of displaying time only.

If individual people want to measure the body temperature, the cardiac beats, or the blood pressure, then they have to procure body thermometers, cardiac beat meters, and blood pressure meters. Further, as to the atmospheric temperature, it can be measured only by an atmospheric air thermometer.

The conventional digital wrist watch contains a high function IC counting element, and displays the current time in numerals.

The IC counting element has various functions such as data calculations, data memorizing, and data withdrawing. Unfortunately, however, the functions are limited to time, and the functions are not applied to other fields.

Further, as the material welfare is promoted, more and more people are becoming concerned with their health. Accordingly, various health checking devices are developed and commercialized, so that people can check their health without going to hospitals.

Generally, the electronic digital body thermometer, the cardiac beat meter, the blood pressure meter and the like contain the same IC counting element, but each of them has to be procured separately. That is, they all have the same basic structure, but all of them have to be procured separately, with the result that the economical burden becomes heavy, as well as being troublesome to procure them. Further, the health devices are bulky, and therefore, their handling and storing are inconvenient.

SUMMARY OF THE INVENTION

The present invention is intended to overcome the above described disadvantages of the conventional technique.

Therefore it is an object of the present invention to provide a health watch which is based on the principle that an electronic digital watch contains a data arithmetic IC element, and that blood vessels pass through the wrist so as to make it possible to check the health, thereby checking the health state by measuring the body temperature, the cardiac beats, the blood pressure and the like to audibly and visually know the health state.

In achieving the above object, the health watch includes an electronic digital watch containing a plurality of known IC counting elements, and the health watch includes: a plurality of display windows arranged on a face of a case of the health watch, the display windows consisting of an atmospheric temperature display window, a body temperature display window, a time display window, a cardiac beat rate display window, a blood pressure display window, and a cardiac beat wavelength display window, and a plurality of IC counting elements being provided to the display windows respectively; a cardiac beating sound speaker formed on one side of the case; a thin and long rubber tube installed on a back face of a band of the case; a body temperature sensor installed on a back face of the case; and a cardiac beat sensor installed on the rubber tube, whereby data of the sensors are inputted and outputted to and from the IC counting elements.

In this manner, one digital health watch can display the atmospheric temperature, the body temperature, the cardiac beat, the cardiac beating sounds, the cardiac beating wavelength, the blood pressure and the like, so that the user can know them audibly and visually.

BRIEF DESCRIPTION OF THE DRAWINGS

The above object and other advantages of the present invention will become more apparent by describing in detail the preferred embodiment of the present invention with reference to the attached drawings in which.

DETAILED DESCRIPTION OF THE PREFERRED EMBODIMENT

Figure 1:
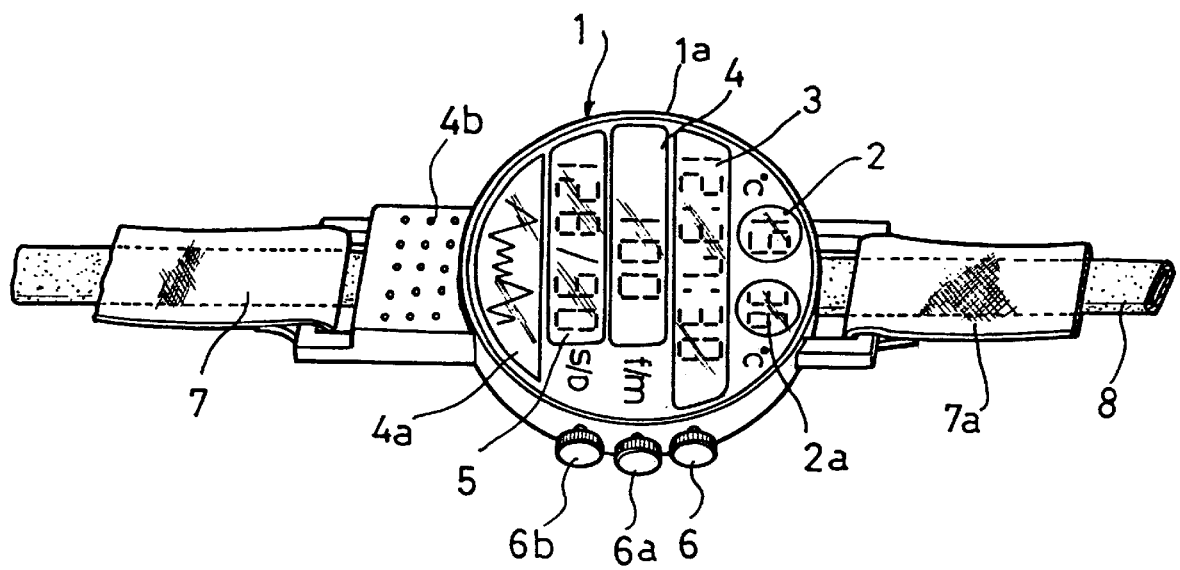
FIG. 1 is a perspective view of the health watch according to the present invention.
Figure 2:
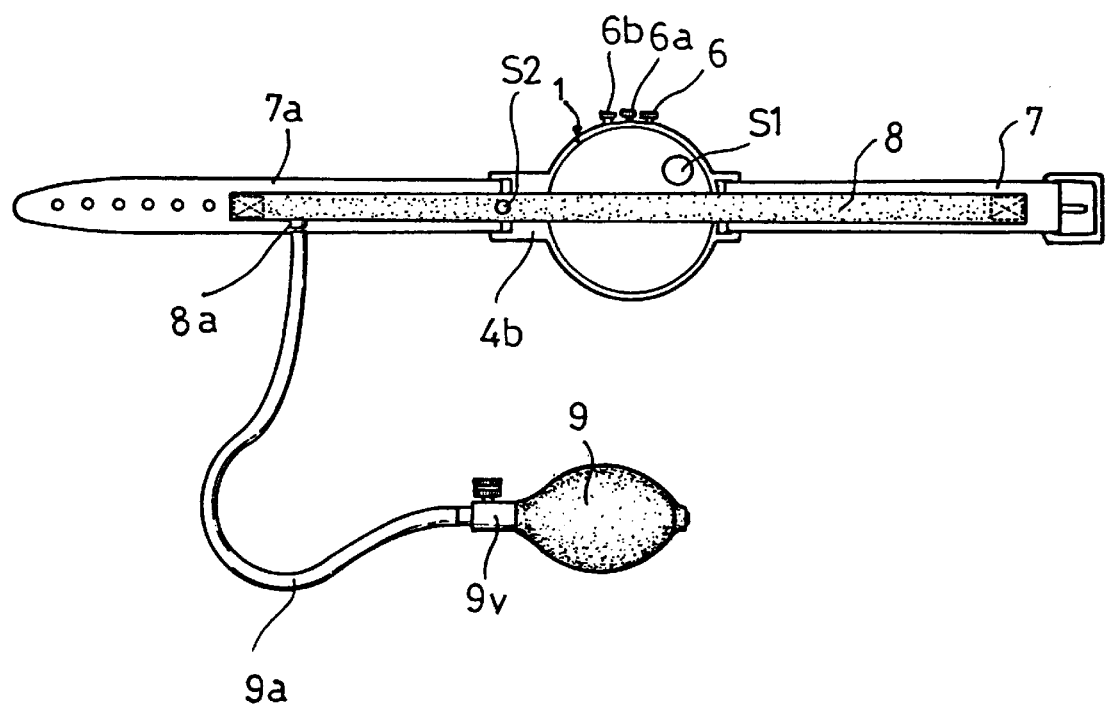
FIG. 2 is a rear perspective view of the health watch according to the present invention.

FIG. 1 is a perspective view of the health watch according to the present invention. FIG. 2 is a rear perspective view of the health watch according to the present invention.

The health watch of the present invention is a kind of electronic digital watch 1 containing a plurality of IC counting elements.

A plurality of display windows are arranged on a face of a case 1a of the health watch 1, the display windows consisting of: an atmospheric temperature display window 2, a body temperature display window 2a, a time display window 3 showing hours, minutes and seconds, a cardiac beat rate display window 4, a blood pressure display window 5 showing the diastolic pressure and the systolic pressure, a cardiac beat wavelength display window 4a, and an IC counting element provided to each of the display windows.

On a side of the case 1a, there protrudes a time displaying knob 6, a cardiac measuring knob 6a, and a blood pressure measuring knob 6b, and these knobs control the IC counting elements. Therefore, when any one of the knobs is manipulated, the relevant function is activated.

Figure 1A:
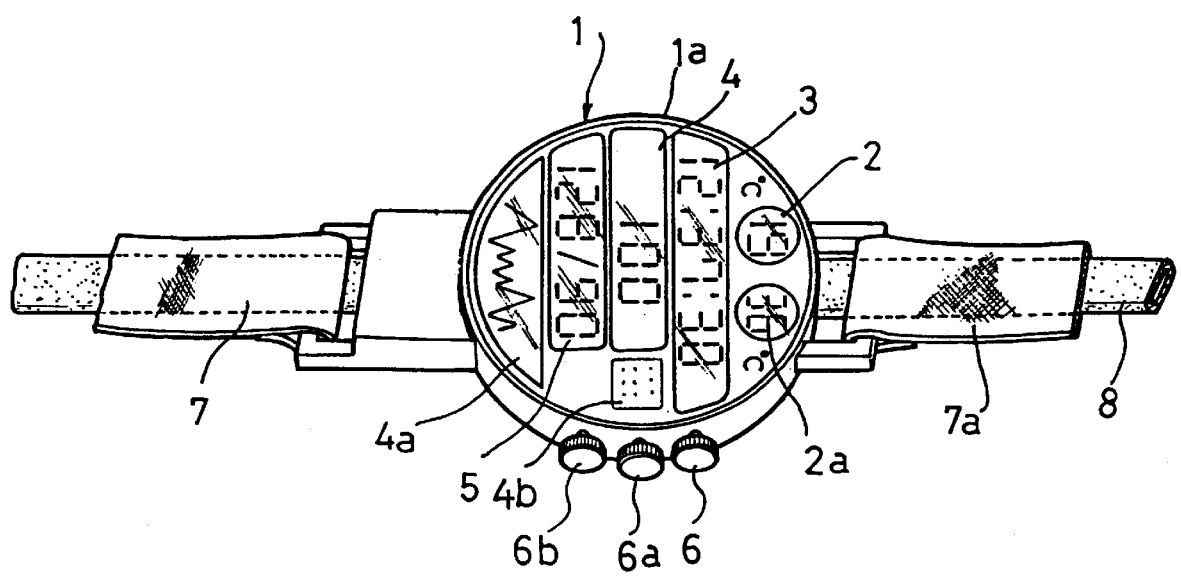
FIG. 1A is a perspective view of a health watch in accordance with an alternate embodiment of the present invention.
Figure 3:
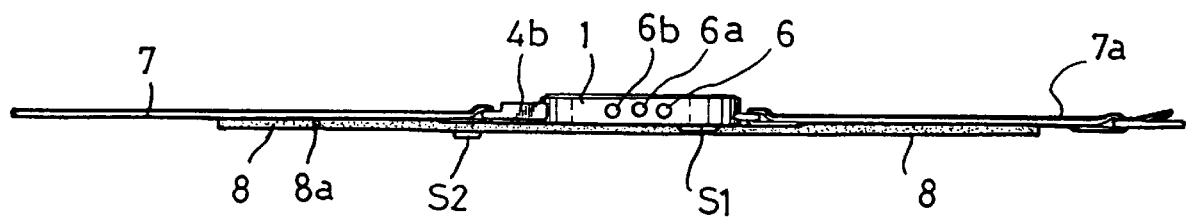
FIG. 3 is a side view of the health watch according to the present invention.

A cardiac beat sound speaker 4b is installed near a band ring of the case 1a, and alternatively this speaker 4b may be installed within the case 1a (see, for example, FIG. 1A).

A long rubber tube 8 extends along the back face of watch bands 7 and 7a and is sealed closed at both ends to form an air bladder and includes an air inlet nipple 8a to make it possible to check the blood pressure. This rubber tube 8 is collapsed flat, but when the blood pressure is to be checked, an air compressing device 9 having a conduit 9a is connected to a nipple 8a to inject air into the rubber tube 8.

The air compressing device 9 is separable from the health watch, and is connected only when the blood pressure is to be checked.

A body temperature sensor S1 is formed on the back of the case 1a to be contacted to the wrist, while a cardiac beat and a blood pressure sensor S2 is installed on a side of the rubber tube 8 in contact with the wrist. Thus the data from the sensors can be supplied to the respective IC counting elements.

An atmospheric temperature sensor is not illustrated in the drawings, but it is installed within the case 1*a*.

The positions of the sensors can be modified in another embodiment, and the rubber tube is not limited to any particular material.

Further, the display windows are not limited to that illustrated in FIG. 1, but they can be modified to various shapes and arrangements.

Now the present invention will be described as to its action.

Hour, minute and second are displayed on the time display window 3 by the output of the IC counting element which is not illustrated in the drawings. The atmospheric temperature is displayed on the atmospheric temperature display window based on the same principle.

When the health watch is worn on the wrist, the body temperature sensor S1 is contacted on the skin of the wrist, and therefore, the temperature data is inputted from the body temperature sensor S1 to the IC counting element to be outputted so as to be displayed on the body temperature display window 2*a*.

Accordingly, the atmospheric temperature and the body temperature can be known visually.

Figure 4:
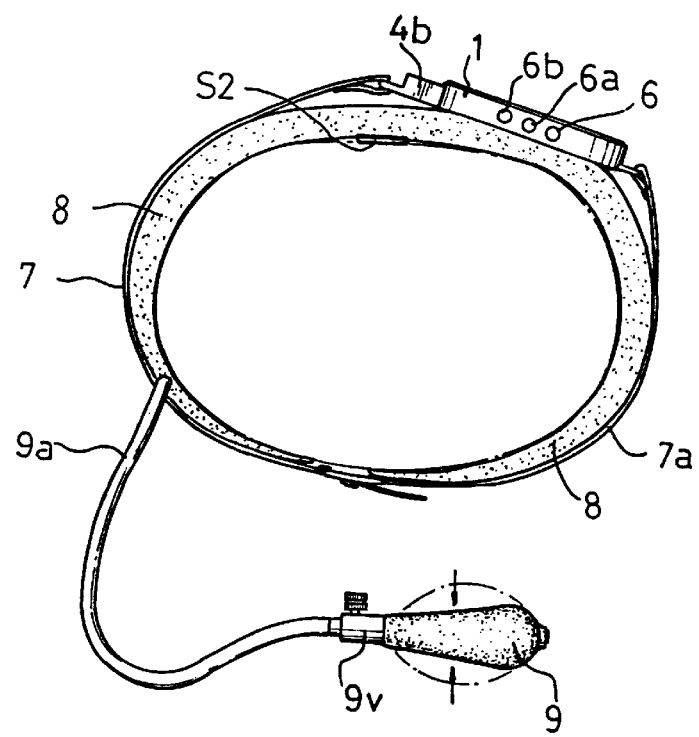
FIG. 4 illustrates the measuring of the blood pressure according to the present invention.

When the cardiac beats and the blood pressure are to be measured, first the cardiac beat measuring knob 6*a* and the blood pressure measuring knob 6*b* are pressed. Then as shown in FIG. 4, the watch band is slightly loosened, then the band is slightly twisted so as for the cardiac beat and blood pressure sensor S2 to be contacted to the blood vessel of the wrist, then the conduit 9*a* of the air compressing device 9 is connected to the nipple 8*a* of the flatly collapsed rubber tube 8, and then, air is injected into the rubber tube 8 by compressing the air compressing device 9.

Then the valve 9*v* of the air compressing device 9 is slowly opened, so that the air of the rubber tube 8 would be discharged, thereby measuring the cardiac beating rate and the blood pressure.

The sensed data are inputted into the IC counting elements to be counted before being displayed. That is, the cardiac beating rate and the diastolic pressure and the systolic pressure are displayed on the cardiac beat rate display window 4 and the blood pressure display window 5 respectively.

The cardiac beating sounds are outputted through the speaker 4*b*, so that they would be audible. The cardiac beat wavelength is visually displayed on the cardiac beat wavelength display window 4*a*.

After the use, if the cardiac beat measuring knob 6*a* and the blood pressure measuring knob 6*b* are pressed again, the figures displayed on the relevant windows are erased, and the measuring functions are terminated.

According to the present invention as described above, a plurality display windows are arranged on a face of a case of the health watch, and the display windows consist of an atmospheric temperature display window, a body temperature display window, a time display window, a cardiac beat rate display window, a blood pressure display window, a cardiac beat wavelength display window, and an IC counting element provided to each of the display windows. Further, a body temperature sensor is installed on a back face of the case, and a cardiac beat sensor is installed on the rubber tube, whereby data sensed by the sensors are inputted and outputted to and from the IC counting elements.

Thus the various functions are combined in one wrist watch, so that a convenience would be ensured by eliminating the troubles of carrying and storing the various conventional separate health checking devices. Therefore, one's own health state can be checked at any place, thereby making it possible to prevent assault of any disease.

What is claimed is:

1. A health watch for use in monitoring the health state of the user and which includes a plurality of high function integrated circuit (IC) counting elements for display of data, the health watch comprising:

a watch case adapted to be worn on the wrist of a user, said watch case having a back face which lies against the user's wrist and a front face provided with a plurality of display windows for display of various data including a cardiac beat rate display window, a blood pressure display window, a cardiac beat wavelength display window and a time display window;

each of said plurality of display windows being provided with a respective one of said plurality of IC counting elements;

an adjustable watch band for securing said watch case to the wrist of the user, said watch band having a backside facing the wrist of the user;

a normally flat rubber tube secured to said backside of said watch band;

a first sensor installed on said rubber tube and operative to detect pulse signals and input as electronic signals to respective ones of said IC counting elements for display on said cardiac beat rate display window, said blood pressure display window and said cardiac beat wavelength display window; and said first sensor located on said rubber tube a sufficient distance from said watch case to permit normal viewing of said front face without substantial wrist rotation being necessary when said first sensor is positioned over the blood vessel of the wrist.

2. The health watch according to claim 1, which further includes a speaker provided to one side of said watch case for audible reproduction of cardiac beats detected by said first sensor.

3. The health watch according to claim 1, which further includes a speaker installed within said watch case for audible reproduction of cardiac beats detected by said first sensor.

4. The health watch according to claim 1, which further includes:

a body temperature display window provided to said watch case front face for display of body temperature data; and a second sensor installed on said watch case back face, said second sensor operative to detect and input body temperature data to the respective IC counting element for display on said body temperature display window.

5. The health watch according to claim 1, wherein said rubber tube includes a nipple adapted to permit connection with a conduit of a separate air compressing device which is employed to inject air into said rubber tube when measuring blood pressure.

6. The health watch according to claim 1, wherein said watch case includes individual control knobs for controlling the function of the respective IC counting elements for display of time, cardiac beat measurements, and blood pressure measurements.

7. A health watch for use in monitoring the health state of the user and which includes a plurality of high function integrated circuit (IC) counting elements for display of data, the health watch comprising:

- a watch case adapted to be worn on the wrist of a user, said watch case having a back face which lies against the user's wrist and a front face provided with a plurality of display windows including a body temperature display window, a cardiac beat rate display window, a blood pressure display window, a cardiac beat wavelength display window and a time display, window;
- each of said plurality of display windows being provided with a respective one of said plurality of IC counting elements;
- a body temperature sensor installed on said watch case back face, said body temperature sensor operative to input body temperature data to a respective IC counting element for display on said body temperature display window;
- an adjustable watch band for securing said watch case to the wrist of the user, said watch band having a backside facing the wrist of the user;
- a normally flat rubber tube secured to said backside of said watch band;
- a cardiac beat and blood pressure sensor installed on said rubber tube and operative to detect pulse signals and input as electronic signals to respective ones of said IC counting elements for display on said cardiac beat rate display window, said blood pressure display window and said cardiac beat wavelength display window; and
- said cardiac beat and blood pressure sensor located on said rubber tube a sufficient distance from said watch case to permit normal viewing of said front face without substantial wrist rotation being necessary when said cardiac beat and blood pressure sensor is positioned over the blood vessel of the wrist.

8. The health watch according to claim 7, which further includes a speaker provided to one side of said watch case for audible reproduction of cardiac beats detected by said cardiac beat and blood pressure sensor.

9. The health watch according to claim 7, which further includes a speaker installed within said watch case for audible reproduction of cardiac beats detected by said cardiac beat and blood pressure sensor.

10. The health watch according to claim 7, wherein said rubber tube includes a nipple adapted to permit connection with a conduit of a separate air compressing device which is employed to inject air into said rubber tube when measuring blood pressure.

11. The health watch according to claim 7, wherein said watch case includes individual control knobs for controlling the function of the respective IC counting elements for display of time, cardiac beat measurements, and blood pressure measurements.

\* \* \* \* \*